(12) United States Patent
Hara et al.

(10) Patent No.: US 11,446,519 B2
(45) Date of Patent: Sep. 20, 2022

(54) CHARGED PARTICLE IRRADIATION APPARATUS

(71) Applicant: B Dot Medical Inc., Tokyo (JP)

(72) Inventors: Yousuke Hara, Tokyo (JP); Takuji Furukawa, Tokyo (JP); Ryohei Tansho, Tokyo (JP)

(73) Assignee: B DOT MEDICAL INC., Tokyo (JP)

( * ) Notice: Subject to any disclaimer, the term of this patent is extended or adjusted under 35 U.S.C. 154(b) by 0 days.

(21) Appl. No.: 17/390,157

(22) Filed: Jul. 30, 2021

(65) Prior Publication Data
US 2022/0062656 A1 Mar. 3, 2022

(30) Foreign Application Priority Data

Sep. 3, 2020 (JP) .............................. JP2020-148135

(51) Int. Cl.
*G21K 1/04* (2006.01)
*A61N 5/10* (2006.01)
(Continued)

(52) U.S. Cl.
CPC ......... *A61N 5/1048* (2013.01); *A61N 5/1045* (2013.01); *G21K 1/02* (2013.01); *G21K 5/04* (2013.01); *A61N 2005/1087* (2013.01)

(58) Field of Classification Search
CPC ................ A61N 5/1048; A61N 5/1045; A61N 2005/1087; G21K 1/02; G21K 5/04; G21K 1/046
See application file for complete search history.

(56) References Cited

U.S. PATENT DOCUMENTS 6,730,924 B1 * 5/2004 Pastyr ...................... G21K 1/04
378/150
6,891,177 B1 5/2005 Kraft et al.
(Continued)

FOREIGN PATENT DOCUMENTS

JP 5-31202 A 2/1993
JP 2007-61438 A 3/2007
(Continued)

OTHER PUBLICATIONS

The Decision to Grant a Patent has been received for JP 2020-148135 dated Jan. 5, 2021.
(Continued)

*Primary Examiner* — Wyatt A Stoffa
(74) *Attorney, Agent, or Firm* — Birch, Stewart, Kolasch & Birch, LLP

(57) ABSTRACT

The invention provides a charged particle irradiation apparatus including: a collimator apparatus provided in an irradiation nozzle that emits a charged particle beam to an irradiation target; and a collimator control unit that controls the collimator apparatus. The collimator apparatus includes a collimator mechanism having one or more arm-shape collimators extending from a base part and a drive mechanism that moves the collimator mechanism on a plane perpendicular to a traveling direction of a charged particle beam. The arm-shape collimator includes one or more movable leaves that rotate independently of each other on the perpendicular plane. By moving the collimator mechanism and/or rotating the movable leaves so that the arm-shape collimators are arranged along a shape of an edge of an irradiation target on the perpendicular plane, the collimator control unit causes the arm-shape collimators to block a charged particle beam that would otherwise irradiate outside of the edge of the irradiation target.

4 Claims, 12 Drawing Sheets

(51) Int. Cl.
*G21K 1/02* (2006.01)
*G21K 5/04* (2006.01)

(56) References Cited

U.S. PATENT DOCUMENTS

| | | | | |
|---|---|---|---|---|
| 7,783,007 | B2* | 8/2010 | Echner | G21K 1/04 |
| | | | | 378/65 |
| 8,831,169 | B2* | 9/2014 | Zaiki | A61B 6/06 |
| | | | | 378/150 |
| 10,617,885 | B2* | 4/2020 | Flynn | A61N 5/1045 |
| 10,658,089 | B2* | 5/2020 | Sharpless | G21K 1/046 |
| 10,818,404 | B2* | 10/2020 | Towe | A61N 5/1045 |
| 2007/0053492 | A1 | 3/2007 | Kidani | |
| 2013/0053617 | A1* | 2/2013 | Pu | A61N 5/1048 |
| | | | | 600/1 |
| 2013/0272504 | A1* | 10/2013 | Deutsch | G21K 1/04 |
| | | | | 378/150 |
| 2015/0174429 | A1* | 6/2015 | Zwart | A61N 5/1083 |
| | | | | 250/396 R |
| 2016/0199667 | A1 | 7/2016 | Flynn et al. | |
| 2017/0157425 | A1 | 6/2017 | Zwart et al. | |
| 2919/0027264 | | 1/2019 | Kamiguchi | |
| 2021/0265071 | A1* | 8/2021 | Rochford | A61N 5/1045 |
| 2021/0393984 | A1* | 12/2021 | Tansho | A61N 5/1071 |

FOREIGN PATENT DOCUMENTS

| | | |
|---|---|---|
| JP | 2014-113215 A | 6/2014 |
| JP | 2016-526452 A | 9/2016 |
| JP | 2018-122156 A | 8/2018 |
| KR | 10-2016-0059534 A | 5/2016 |
| KR | 10-2017-0029348 A | 3/2017 |
| WO | WO 2005/048846 A1 | 6/2005 |

OTHER PUBLICATIONS

Korean Notice of Allowance for Korean Application No. 10-2021-0093642, dated Sep. 1, 2021.

Japanese Notice of Reasons for Refusal (including an English translation thereof) issued in the corresponding Japanese Patent Application No. 2020-148135 dated Dec. 1, 2020.

Extended European Search Report for European Application No. 21188725.2, dated Jan. 20, 2022.

* cited by examiner

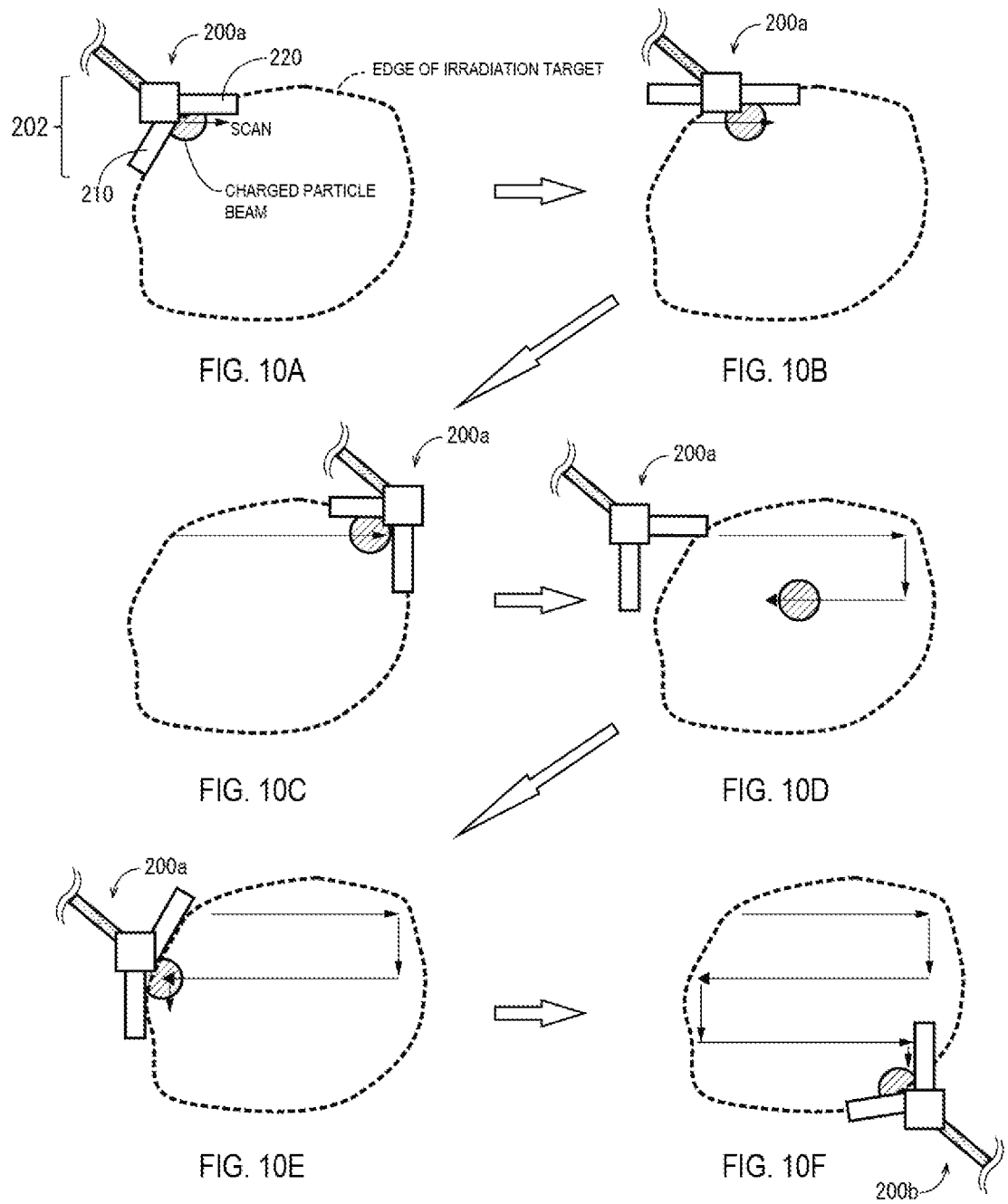

CHARGED PARTICLE IRRADIATION APPARATUS

BACKGROUND OF THE INVENTION

Field of the Invention

The present invention relates to a charged particle irradiation apparatus that performs scanning with a charged particle beam and irradiates an irradiation target spot by spot (referred to as "scanning irradiation").

Description of the Related Art

Conventionally, particle therapy treatment to irradiate a malignant tumor such as a cancer with a charged particle beam (also referred to as "particle beam") accelerated by high energy and treat the malignant tumor has been employed. In recent years, in particle therapy treatment using a charged particle beam such as a proton beam or a carbon beam, a new irradiation method called scanning irradiation has been paid attention, and the number of facilities that implement the scanning irradiation has increased. In the conventional particle therapy treatment, a broad beam irradiation method that statically expands a charged particle beam that is thin in the lateral direction (irradiation slice plane direction) and the traveling direction (length (depth) direction) by using various irradiation field forming devices (for example, a scatterer, a ridge filter, a collimator, or a patient bolus) is the mainstream. In the scanning irradiation method, however, a charged particle beam is three-dimensionally, dynamically controlled to form an irradiation field without using such an irradiation field forming device, and therefore improvement of a dose distribution to an irradiation target is expected. The particle therapy treatment using the scanning irradiation method is to scan a tumor with a charged particle beam and does not require a multi-leaf collimator for matching a spread beam to a tumor contour.

Japanese Patent Application Laid-Open No. 2018-536522 discloses a method of driving the multi-leaf collimator itself to improve dose distribution of the edge of an irradiation target with a smaller number of leaves than in the conventional case. Japanese Patent Application Laid-Open No. 2016-526452 discloses an apparatus that uses dynamic trimming collimator to block only the beam irradiating an irradiation target edge and improves sharpness (edgy outline) of a dose distribution. Although the multi-leaf collimator disclosed in Japanese Patent Application Laid-Open No. 2018-536522 has an opening shape that is variable in accordance with the shape of an irradiation target and can reproduce tumor shapes of respective patients, drive control becomes more complex proportionally to the number of leaves (FIG. 12).

A scanning irradiation apparatus is disclosed in "A dynamic collimation system for penumbra reduction in spot-scanning proton therapy: Proof of concept", Daniel E. Hyer, et al., Med. Phys. 41(9), 2014. This apparatus cuts out an edge of the irradiation region by controlling operations of four trimmers independently that are assembled in a rectangular shape on a plane perpendicular to a beam where the beam passes.

In a particle therapy treatment using a scanning irradiation apparatus, there is a demand for improving sharpness (penumbra) of a dose distribution of a charged particle beam at the edge of an irradiation target in order to reduce influence on a normal tissue outside the irradiation target as small as possible while enhancing dose concentration on a tumor that is the irradiation target.

Although, as disclosed in Japanese Patent Application Laid-Open No. 2016-526452 or the above reference by Daniel E. Hyer, et al., there is a method of blocking a charged particle beam at an irradiation target edge with a reduced number of leaves of a collimator, it is difficult to change the shape made with leaves to sufficiently match the shape of the edge of an irradiation target, and in particular, this tendency becomes notable as the shape of the irradiation target becomes more complex.

SUMMARY OF THE INVENTION

In view of the above, the present invention intends to provide a charged particle irradiation apparatus that has a collimator apparatus provided in an irradiation nozzle configured to emit a charged particle beam to an irradiation target and performs a scan with the charged particle beam to irradiate the irradiation target spot by spot.

The present invention includes the following aspects [1] to [6]:

[1] A charged particle irradiation apparatus (10) that performs a scan with a charged particle beam to irradiate an irradiation target spot by spot, the charged particle irradiation apparatus including:

a collimator apparatus (100, 300) provided in an irradiation nozzle (50) that emits a charged particle beam to an irradiation target; and a collimator control unit that controls the collimator apparatus, wherein the collimator apparatus includes a collimator mechanism (102, 302) having one or more arm-shape collimators (110, 120, 310, 320) extending from a base part (106, 306), and a drive mechanism (101) that moves the collimator mechanism on a plane (YZ plane) perpendicular to a traveling direction (X-axis direction) of a charged particle beam, wherein the one or more arm-shape collimators include a plurality of movable leaves that rotate independently of each other on the perpendicular plane (YZ plane), and wherein by moving the collimator mechanism and/or rotating the movable leaves so that the one or more arm-shape collimators are arranged along a shape of an edge of an irradiation target on the perpendicular plane (YZ plane), the collimator control unit causes the one or more arm-shape collimators to block a charged particle beam that would otherwise irradiate outside of the edge of the irradiation target.

[2] The charged particle irradiation apparatus according to [1], wherein the one or more arm-shape collimators are at least two arm-shape collimators (110, 120) extending from the base part, and each of the arm-shape collimators comprises a plurality of the movable leaves connected to each other in series, and wherein by moving the collimator mechanism and/or rotating the movable leaves, respectively, so that the arm-shape collimators are arranged along a shape of an edge of an irradiation target, the collimator control unit causes the one or more arm-shape collimators to block a charged particle beam that would otherwise irradiate outside of the edge of the irradiation target.

[3] The charged particle irradiation apparatus according to [2], wherein the charged particle irradiation apparatus includes at least two the collimator apparatuses, and wherein by moving the collimator mechanisms, respectively, and/or rotating the movable leaves, respectively, so that each of the arm-shape collimators of the collimator apparatuses are arranged in cooperation along the whole shape of an edge of an irradiation target, the collimator control unit causes each of the arm-shape collimators to block a charged particle beam that would otherwise irradiate outside of the edge of the irradiation target.

[4] A charged particle irradiation apparatus (10) that performs a scan with a charged particle beam to irradiate an irradiation target spot by spot, the charged particle irradiation apparatus including:

a collimator apparatus (200) provided in an irradiation nozzle (50) that emits a charged particle beam to an irradiation target; and a collimator control unit that controls the collimator apparatus, wherein the collimator apparatus includes a collimator mechanism (202) including two arm-shape collimators (210, 220) extending from a base part (106), and a drive mechanism (101) that moves the collimator mechanism on a plane (YZ plane) perpendicular to a traveling direction (X-axis direction) of a charged particle beam, wherein each of the two arm-shape collimators includes a movable leaf that rotates on the perpendicular plane (YZ plane), wherein by moving the collimator mechanism and/or rotating the movable leaf so that the arm-shape collimators are arranged along a shape of an edge of an irradiation target on the perpendicular plane (YZ plane), the collimator control unit causes the arm-shape collimators to block a charged particle beam that would otherwise irradiate outside of the edge of the irradiation target, and wherein when an edge of an irradiation target is irradiated with a charged particle beam, the collimator control unit causes the arm-shape collimators to block a charged particle beam that would otherwise irradiate outside of the edge of the irradiation target by moving the collimator mechanism to follow a scan of irradiation spots.

[5] The charged particle irradiation apparatus according to [4], wherein when an irradiation target is irradiated with a charged particle beam, the collimator control unit causes the arm-shape collimators to block a charged particle beam that would otherwise irradiate outside of the edge of the irradiation target by moving the collimator mechanism to follow a scan of irradiation spots and rotating the movable leaf.

[6] The charged particle irradiation apparatus according to any one of [1] to [3], wherein the arm-shape collimator includes a plurality of movable leaves (311 to 313, 321 to 323) connected to the base part and arranged adjacently in the traveling direction (X-axis direction), and wherein each of the movable leaves has at least one joint part (315) and is configured to rotate about the joint part.

BRIEF DESCRIPTION OF THE DRAWINGS

FIGS. 10A-10F are diagrams illustrating that the collimator apparatus follows a scan with a charged particle beam.

DESCRIPTION OF THE EMBODIMENTS

First Embodiment

The first embodiment of the present invention relates to a charged particle irradiation apparatus that has a collimator apparatus provided in an irradiation nozzle and performs a scan with a charged particle beam to irradiate the irradiation target spot by spot. A collimator mechanism of the collimator apparatus has at least one arm-shape collimator extending from a base part, and each arm-shape collimator is formed of a plurality of movable leaves connected to each other in series. Respective movable leaves of the arm-shape collimator rotate independently of each other on a plane perpendicular to a traveling direction of a charged particle beam. This enables the arm-shape collimator to change the shape thereof so as to be arranged along the shape of the edge of an irradiation target. This prevents a charged particle beam from irradiating outside of the irradiation target when the charged particle beam irradiates the edge of the irradiation target by scanning irradiation and improves the sharpness of a dose distribution of the charged particle beam at the edge of the irradiation target. Note that blocking or prevention of a charged particle beam includes a case where irradiation is reduced to the extent that an adversary effect due to a charged particle beam to a healthy site outside an irradiation target is suppressed without being limited to a case where irradiation with a charged particle beam is fully blocked or prevented.

Charged Particle Irradiation Apparatus 10

Figure 1:
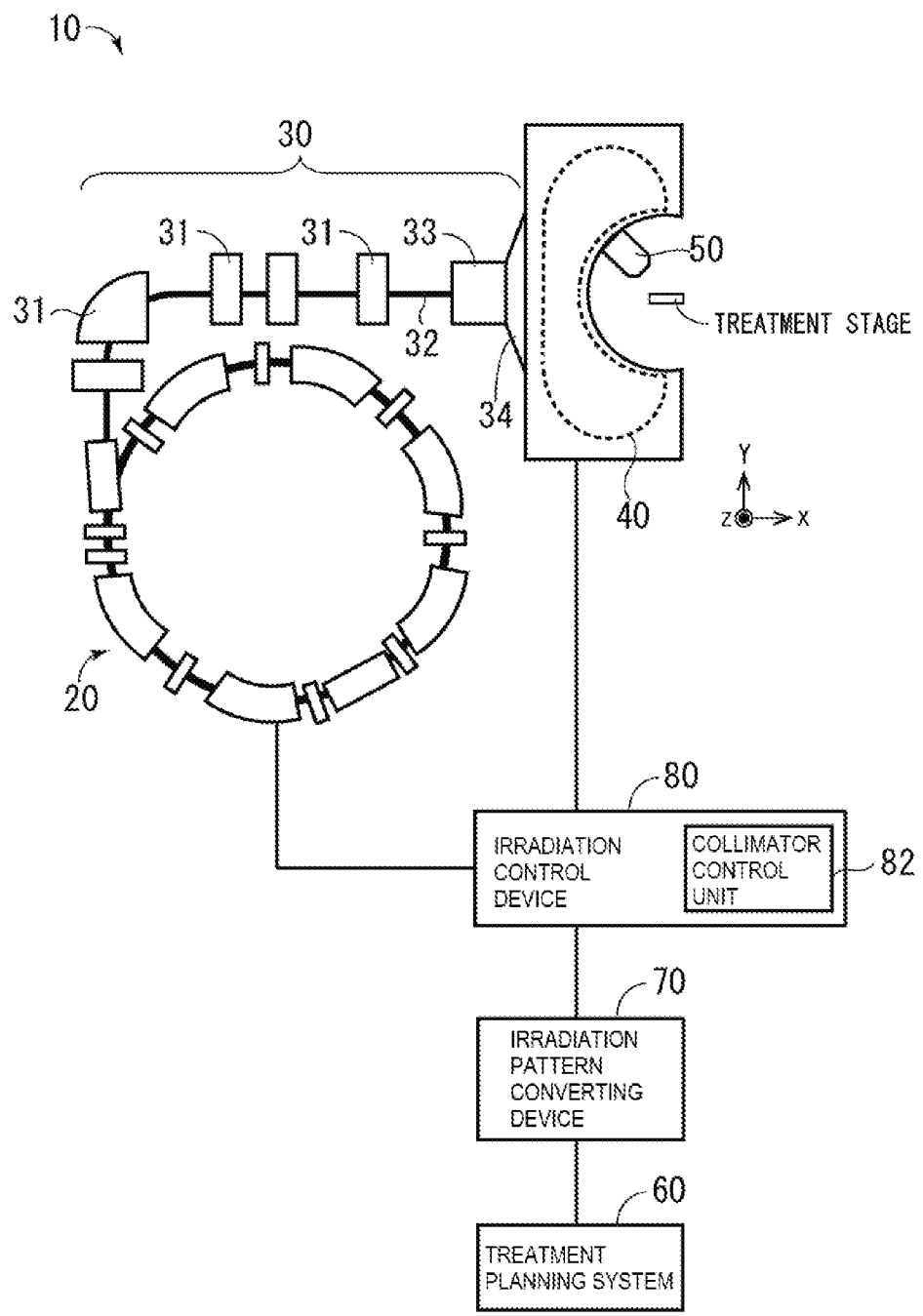
FIG. 1 is a schematic diagram of a configuration of a charged particle irradiation apparatus according to a first embodiment.
Figure 2A:
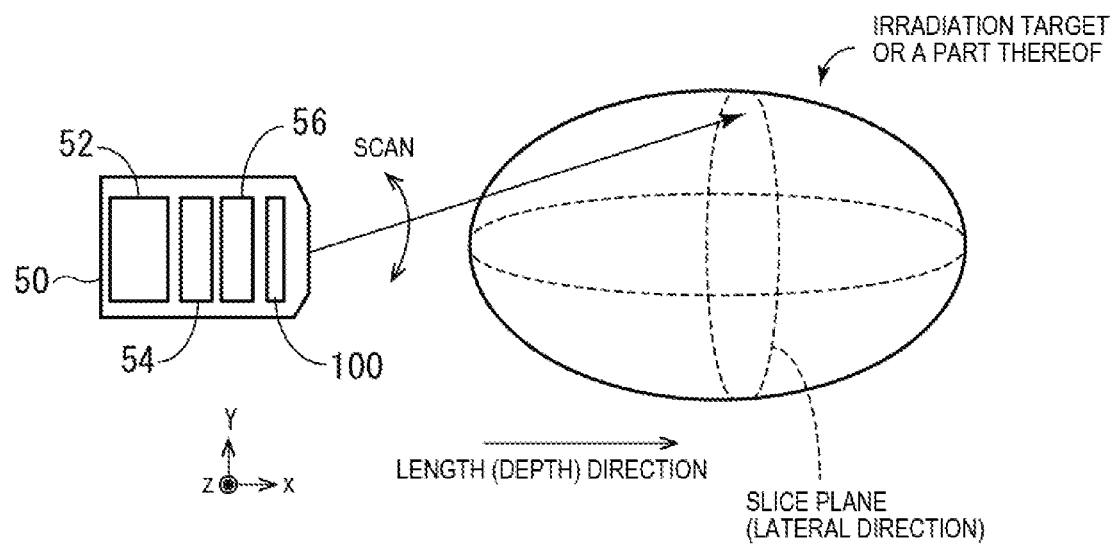
FIG. 2A and FIG. 2B are diagrams of the overview of an irradiation nozzle and scanning irradiation.
Figure 2B:
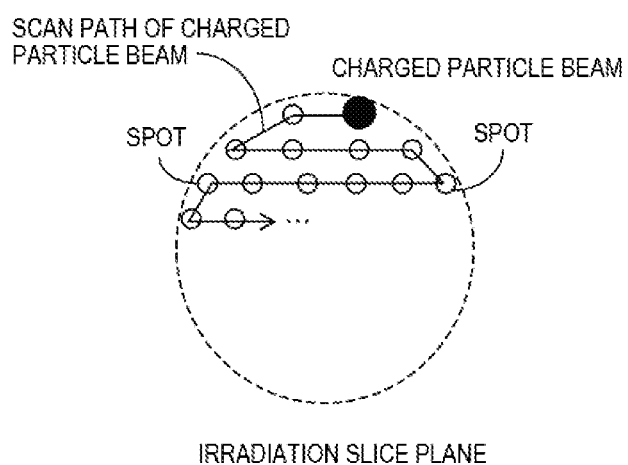

FIG. 1 is a schematic diagram of a configuration of a charged particle irradiation apparatus 10, and FIG. 2A and FIG. 2B are diagrams of the overview of an irradiation nozzle 50 and scanning irradiation.

The charged particle irradiation apparatus 10 has an accelerator 20, a charged particle beam transport system 30, a focusing magnet 40, and the irradiation nozzle 50. Further, the charged particle irradiation apparatus 10 has a treatment planning system 60, an irradiation pattern converting device 70, and an irradiation control device 80. The irradiation control device 80 includes a collimator control unit 82 that controls a collimator apparatus described later.

The accelerator 20 is a device that generates a charged particle beam, which is a synchrotron, a cyclotron, or a linear accelerator, for example. The charged particle beam generated by the accelerator 20 is guided to the focusing magnet 40 through the charged particle beam transport system 30.

The charged particle beam transport system 30 includes one or a plurality of charged particle beam adjustment units 31, a vacuum chamber 32, a bending magnet 33, a sector-shaped vacuum chamber 34, and the like. The accelerator 20, the charged particle beam adjustment units 31, and the bending magnet 33 are connected via the vacuum chambers 32, and the bending magnet 33 and the focusing magnet 40 are connected via the sector-shaped vacuum chamber 34. The charged particle beam adjustment units 31 includes a beam slit used for adjusting the beam shape and/or the dose of a charged particle beam, an electromagnet used for adjusting the traveling direction of a charged particle beam, a quadrupole magnet used for adjusting the beam shape of a charged particle beam, a steering magnet used for fine-tuning the beam position of a charged particle beam, and the like as appropriate in accordance with the specification.

The bending magnet 33 continuously deflects a charged particle beam at the deflection angle ($\phi$) and launches the charged particle beam to the focusing magnet 40. When the traveling direction of a charged particle beam is defined as an X-axis, the direction of a magnetic field generated by the focusing magnet 40 is defined as a Z-axis, and the direction orthogonal to the X-axis and the Z-axis is defined as a Y-axis, the focusing magnet 40 converges a charged particle beam, which is incident from a wide range of a deflection angle ($\phi$) relative to the X-axis, into the isocenter (O) at an irradiation angle ($\theta$) on the XY plane through the irradiation nozzle 50. The bending magnet 33 and the focusing magnet 40 are those described in prior patent documents (Japanese Patent No. 6364141, Japanese Patent No. 6387476, or Japanese Patent No. 6734610) filed by the present applicant, which is incorporated herein by reference, and detailed description thereof is omitted.

The irradiation nozzle 50 is located inside a treatment room in which treatment using a charged particle beam or the like are performed and irradiates an irradiation target with a charged particle beam. The irradiation nozzle 50 continuously moves along the shape on the exit side of an effective magnetic field region generated by the focusing magnet 40 on the XY plane. The charged particle beam traveling from the exit side of the effective magnetic field region to the isocenter passes inside the irradiation nozzle 50, and a scan with the charged particle beam is performed by the irradiation nozzle 50.

Note that, with respect to a difference between adjustment of the irradiation position using a change of the irradiation angle ($\theta$) and adjustment of the irradiation position using a scan with a charged particle beam performed by a scanning magnet 52 inside the irradiation nozzle 50, it can be understood that relatively coarse adjustment of the irradiation position of a charged particle beam is performed with a change of the irradiation angle $\theta$, and relatively fine adjustment (fine tune) of the irradiation position of a charged particle beam is performed with a scan with a charged particle beam by a scanning magnet 52, although not limited thereto. In both cases, adjustment of the irradiation position in the length (depth) direction of an irradiation target can be performed by changing the energy of the charged particle beam.

The irradiation nozzle 50 has the scanning magnet 52, a dose monitor 54, a position monitor 56, and a collimator apparatus 100. Note that the collimator apparatus 100 may be in a form of being installed upstream (on the focusing magnet 40 side) that is between the scanning magnet 52 and the dose monitor 54 without being limited to a form of being installed downstream (on the irradiation target side) of the position monitor 56. Further, the energy of a charged particle beam may be adjusted by further providing an energy adjustment unit such as a range shifter to the irradiation nozzle 50, may be adjusted on the accelerator 20 side, or may be adjusted by both of the above.

By adjusting the amount of flowing current or the direction of the current of the scanning magnet 52, it is possible to fine-tune the traveling direction of a charged particle beam launched from the irradiation nozzle 50, change the irradiation position of the charged particle beam, and perform a scan (scanning) of the charged particle beam.

The dose monitor 54 is an ionization chamber that monitors a charged particle beam and measures the dose of the charged particle beam. The ionization chamber is a radiation detector in which two-polarity electrodes are installed inside a container filled with a gas. When an ionized radiation such as charged particles enters the ionization chamber, the internal gas is ionized into electrons and positive ions. A voltage is applied between electrodes inside the ionization chamber, the ionized electrons and positive ions move to the positive electrode and the negative electrode, respectively, and current occurs. This current is measured, and thereby the dose of a charged particle beam is measured.

The position monitor 56 measures the position of a passing charged particle beam and measures the position of a charged particle beam at an irradiation target. Details of the collimator apparatus 100 will be described later.

In the scanning irradiation, an irradiation target is sectioned into a plurality of slice layers (also referred to as slice planes), and each slice plane is divided into a plurality of irradiation spots. In general, the number of irradiation spots may be up to several ten thousands even for a typical irradiation target size (several hundreds $cm^3$). The position of a charged particle beam is adjusted by the scanning magnet 52, and irradiation is performed as if irradiation spots are filled one by one (FIG. 2B). The position of the charged particle beam is measured by the position monitor 56, and the dose to each irradiation spot is measured by the dose monitor 54. When the dose value measured by the dose monitor 54 reaches a preset value (planned dose) set in advance by a medical worker such as a medical doctor for each irradiation spot (irradiation completion), the charged particle beam is moved to the next irradiation spot position. When irradiation to all the irradiation spots within one slice plane ends, the irradiation of the charged particle beam is temporarily stopped, and irradiation of the next slice plane (in the depth direction) is then prepared. The entire irradiation target is irradiated with the charged particle beam by repetition of the above flow, and when all the irradiation spots of the irradiation target are finally irradiated with a planned dose, the beam irradiation is completely stopped, and the treatment ends.

When a different slice plane is irradiated, the energy of a charged particle beam is changed. The change of energy can be performed by changing the output of the accelerator 20 to change the energy of a charged particle beam or using an energy adjustment unit such as a range shifter for the irradiation nozzle 50. In response to completion of setting for energy change, irradiation of a charged particle beam in the next slice is started. The entire irradiation target is irradiated by repetition of the above flow, and when irradiation of the planned doses set for all the irradiation spots of the irradiation target is finally completed, the irradiation of the charged particle beam is stopped.

The treatment planning system 60 generates treatment plan data based on input from a medical worker and transmits the generated treatment plan data to the irradiation pattern converting device 70. The treatment plan data is generated by a medical worker defining the region of a tumor (irradiation target) based on a CT image and/or an MRI image of a patient secured on a treatment stage of a treatment room to assign the tumor shape, assigning an irradiating dose, a dose rate, and the like, or the like in the treatment planning system 60.

The treatment plan data includes information on a dose rate and a dose of a charged particle beam for each irradiation spot and irradiation spot positions (coordinates). The treatment plan data may further include information on energy and a beam size of a charged particle beam for each irradiation spot, a position and a size of a tumor (irradiation target), an irradiation field (an irradiation angle or the like) of a charged particle beam to a tumor, or the like.

Herein, information handled in the treatment plan data is based on CT image information, MRI image information, or the like on a patient and thus is unable to be used directly for irradiation by the charged particle irradiation apparatus 10 or the like, for example. Therefore, conversion from treatment plan data into irradiation control data is required. For example, in the treatment plan data, values of a dose, a dose rate, energy, and the like for each irradiation spot are determined so as to provide a planned dose to an irradiation target. In the actual irradiation, since a dose inside an irradiation target, that is, inside a patient body is unable to be measured, the dose monitor 54 using an ionization chamber serves such a function. The dose monitor 54 is formed of an ionization chamber and a circuit such as an electrometer. Current ionized by a charged particle beam that has passed through the ionization chamber is converted into a corresponding frequency by the circuit and output as a pulse signal, and the dose monitor 54 counts the pulse signal. Therefore, the dose for each irradiation spot in the treatment plan data is handled in a unit specific to radiation therapy that is called a monitor unit (MU) in irradiation control data and associates a count value of pulse signals with a dose.

The irradiation pattern converting device 70 generates irradiation control data based on treatment plan data received from the treatment planning system 60 and transmits the generated irradiation control data to the irradiation control device 80. In the scanning irradiation method, various parameters such as a dose rate, a dose, energy, and the like of a charged particle beam in the irradiation control data are set spot by spot. At this time, as with the invention disclosed in Japanese Patent Application Laid-Open No. 2020-104390 (the content of this application is incorporated herein by reference), correction to measurement values from the dose monitor 54 may be performed spot by spot. The irradiation control data includes control information on the accelerator 20, the charged particle beam transport system 30, the focusing magnet 40, and the irradiation nozzle 50 (for example, a power supply current value of the accelerator 20, current control of the charged particle beam transport system 30 and the focusing magnet 40, drive control of the irradiation nozzle 50, drive control of the collimator apparatus 100, and the like) and the like.

The irradiation control device 80 controls the accelerator 20, the charged particle beam transport system 30, the focusing magnet 40, and the irradiation nozzle 50 to control irradiation of an irradiation target with a charged particle beam in accordance with scanning irradiation based on irradiation control data received from the irradiation pattern converting device 70 and performs treatment by using a charged particle beam in accordance with the scanning irradiation method. Further, the irradiation control device 80 includes the collimator control unit 82 that controls the collimator apparatus 100 of the irradiation nozzle 50.

Collimator Apparatus 100

The collimator apparatus 100 according to the present embodiment will be described with reference to FIG. 3. FIG. 3 is a diagram of the collimator apparatus 100 provided to the irradiation nozzle 50 when viewed from the downstream to the upstream. The collimator apparatus 100 is configured to block a charged particle beam that would otherwise irradiate outside of the edge of the irradiation target (spread out of the edge) of an irradiation target on each slice plane within the YZ plane.

In the present embodiment, the collimator apparatus 100 provided in the irradiation nozzle 50 includes a first collimator apparatus 100a and a second collimator apparatus 100b. Note that only one collimator apparatus 100 may be used in the irradiation nozzle 50, or three or more collimator apparatuses 100 may be used in the irradiation nozzle 50.

The first and second collimator apparatuses 100a and 100b are arranged at positions symmetrical with each other about the center C of the irradiation nozzle 50 (and/or a possible passage region of a charged particle beam) when viewed from the front of the sheet of FIG. 3. The first and second collimator apparatuses 100a and 100b are controlled by the collimator control unit 82 of the irradiation control device 80.

The first collimator apparatus 100a is configured to block a charged particle beam passing mainly through the first quadrant, the second quadrant, and the third quadrant about the center C when viewed from the front of the sheet of FIG. 3. The second collimator apparatus 100b is configured to block a charged particle beam passing mainly through the first quadrant, the third quadrant, and the fourth quadrant about the center C when viewed from the front of the sheet of FIG. 3.

Note that the arrangement of the first collimator apparatus 100a and the second collimator apparatus 100b is not limited to the above, and a case where the first collimator apparatus 100a is arranged in the first quadrant and the second collimator apparatus 100b is arranged in the third quadrant may be possible. Further, without being limited to the case where the first and second collimator apparatuses 100a and 100b are arranged symmetrically with each other about the center C, arrangement positions are adjusted to any positions as long as a charged particle beam can be blocked at the edge of an irradiation target.

The first and second collimator apparatuses 100a and 100b each have a drive mechanism 101 and a collimator mechanism 102.

The drive mechanism 101 moves the collimator mechanism 102 on the YZ plane perpendicular to the traveling direction (X-axis direction) of a charged particle beam. The drive mechanism 101 has a first drive unit 103 that moves along a guide provided in the Z-axis direction, a second drive unit 104 that moves along a guide provided in the Y-axis direction, and a third drive unit 105 that moves in the Y-axis and Z-axis directions along guides that moves together with the first and second drive units 103 and 104. Each of the first to third drive units 103 to 105 has an actuator such as a motor used for moving itself along the guide and is controlled by the collimator control unit 82 of the irradiation control device 80.

The collimator mechanism 102 has a base part 106 connected to the third drive unit 105 and configured to rotate and/or move in a radial direction (radius direction) with respect to the third drive unit 105 in the YZ plane and arm-shape collimators 110 and 120 extending from both sides of the base part 106. Each of the arm-shape collimators 110 and 120 has a plurality of movable leaves connected to each other in series. The position of the base part 106 and rotation of respective movable leaves of the arm-shape collimators 110 and 120 are controlled by the collimator control unit 82 of the irradiation control device 80.

The base part 106 and respective movable leaves of the arm-shape collimators 110 and 120 are metal (iron, brass, lead, or the like) members having a sufficient thickness to block a charged particle beam. The thickness (in the X-axis direction) of a single movable leaf is, but not limited to, 1 cm to 10 cm, and the width (in the longitudinal direction) in the side direction (YZ plane) is, but not limited to, 1 cm to 3 cm.

Figure 3A:
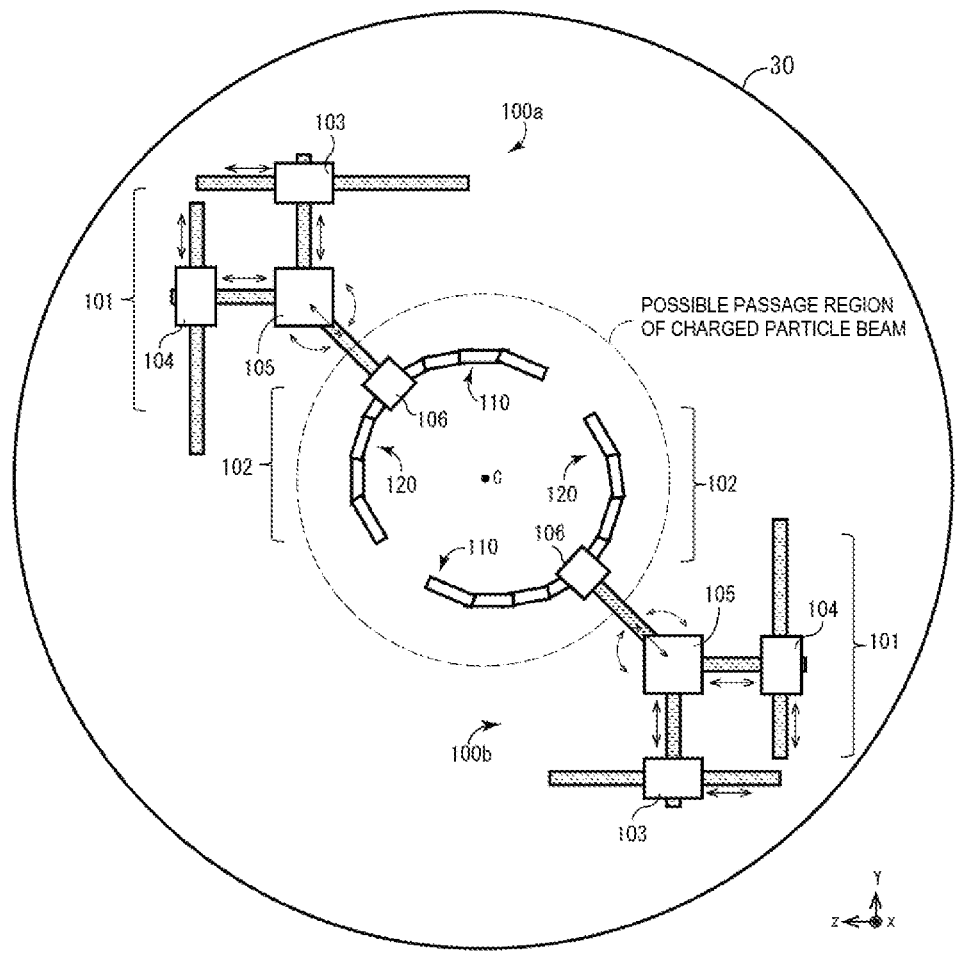
FIG. 3A and FIG. 3B are schematic diagrams of a configuration of a collimator apparatus.
Figure 3B:
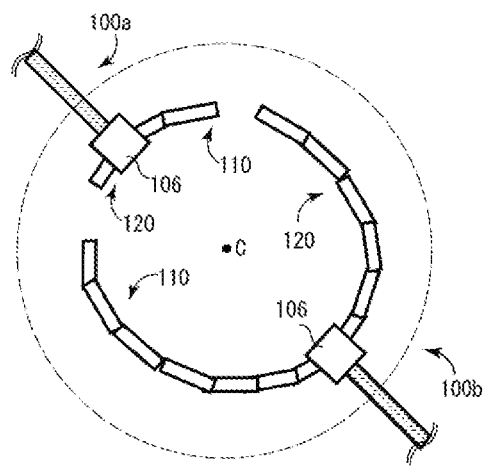

Note that, although the numbers of movable leaves included in respective arm-shape collimators 110 and 120 are the same and the numbers of movable leaves included in respective first and second collimator apparatuses 100a and 100b are also the same in FIG. 3A, these numbers are not limited thereto. For example, as illustrated in FIG. 3B, the numbers of movable leaves included in the arm-shape collimators 110 and 120 may be different from each other, and the numbers of movable leaves included in respective first and second collimator apparatuses 100a and 100b may also be different from each other.

Figure 4A:
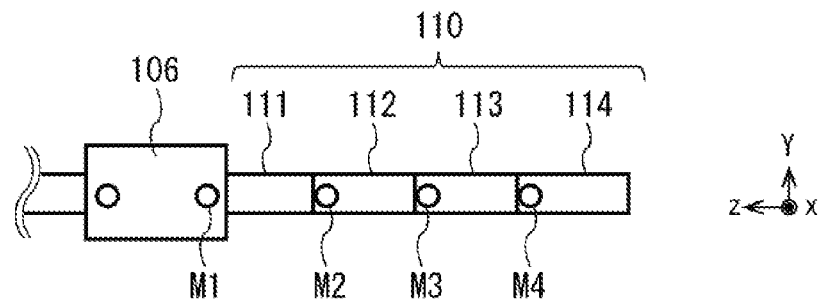
FIG. 4A to FIG. 4C are diagrams illustrating the operation of an arm-shape collimator.

FIG. 4 illustrates the base part 106 and movable leaves 111 to 114 of the arm-shape collimator 110. The base part 106 and the movable leaves 111 to 114 have actuators M1 to M4 such as motors, respectively, so as to be able to rotate independently of each other on the YZ plane while the series connection thereof is maintained.

Figure 4B:
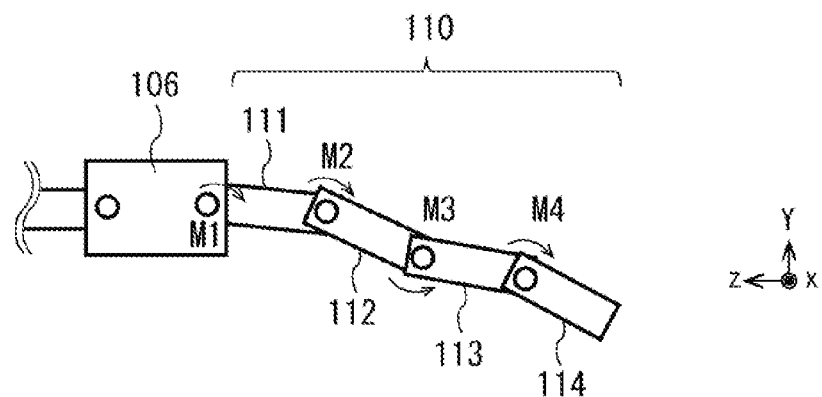
Figure 4C:
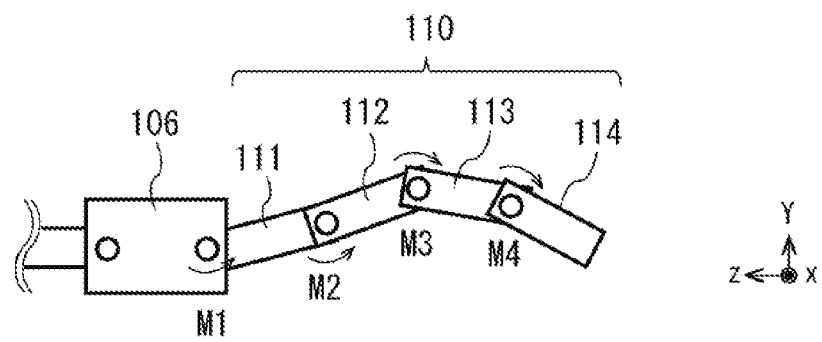

FIG. 4B and FIG. 4C illustrate examples in which the movable leaves 111 to 114 each rotate to the right or the left independently of each other. The collimator control unit 82 of the irradiation control device 80 controls the actuators M1 to M4 of respective movable leaves 111 to 114 independently, and the movable leaves 111 to 114 are rotated independently, respectively, and the shape of the arm-shape collimator can be changed into a desired shape.

Figure 5:
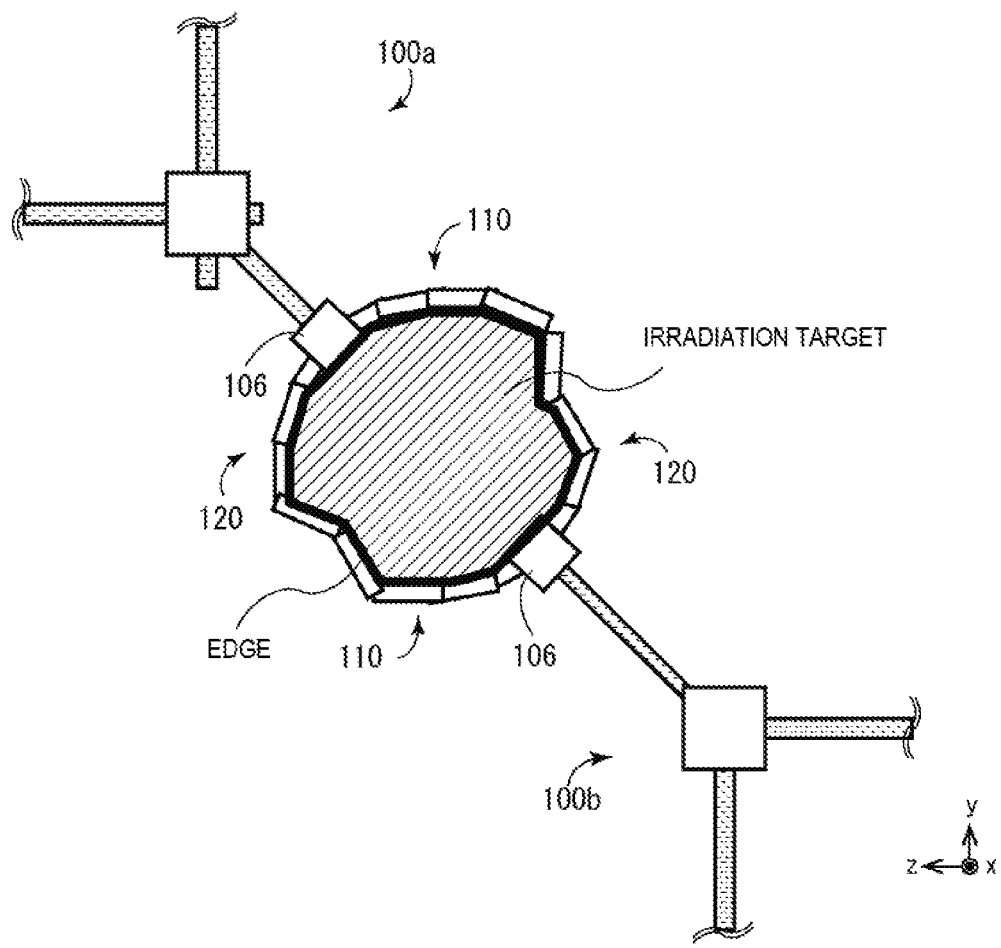
FIG. 5 is a diagram illustrating that the arm-shape collimator is formed along an edge of an irradiation target.

In such a way, the collimator apparatus 100 causes the drive mechanism 101 to move the base part 106 to a desired position in accordance with control of the collimator control unit 82 of the irradiation control device 80 and further adjust the orientation of each movable leaf 110. Accordingly, as illustrated in FIG. 5, for example, the collimator apparatus 100 moves each movable leaf of the arm-shape collimators 110 and 120 of the collimator mechanism 102 to adjust the arm-shape collimators 110 and 120 to be arranged in cooperation along the edge of an irradiation target.

Figure 6:
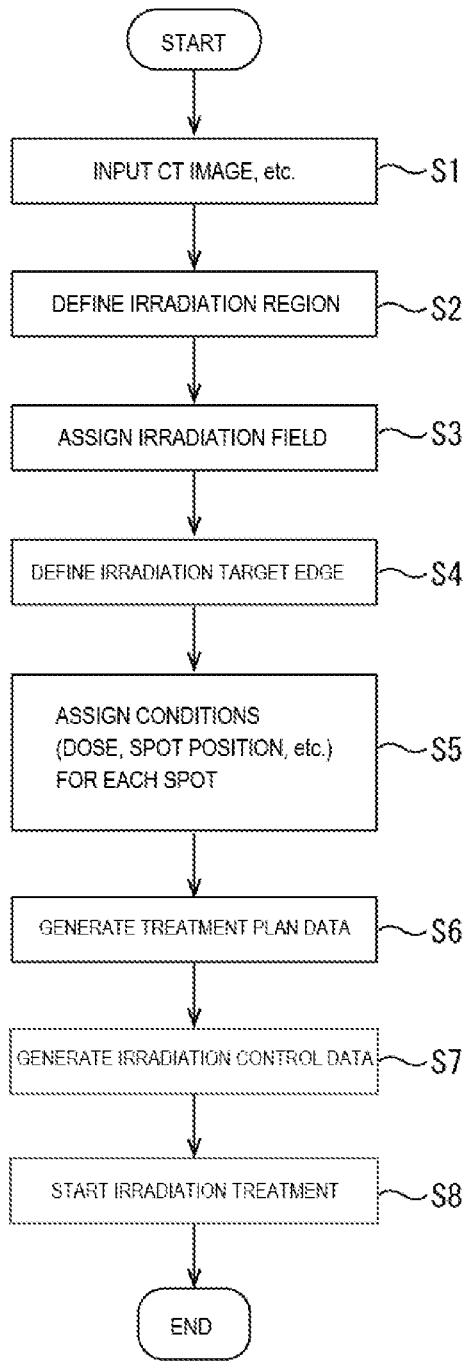
FIG. 6 is a flowchart of particle therapy treatment.

FIG. 6 is a flowchart of a particle therapy treatment in the present embodiment using the charged particle irradiation apparatus 10 that performs scanning irradiation.

First, a CT image and/or an MRI image of a patient secured on a treatment stage in the treatment room is acquired by a medical worker such as a medical doctor or a clinical laboratory technician, and the information thereon is transmitted to the treatment planning system 60 (step S1). In the treatment planning system 60, the region and the shape of a tumor (irradiation target) are defined by the medical worker based on the CT image and/or the MRI image (step S2), and the irradiation angle of a charged particle beam is assigned (step S3).

In the treatment planning system 60, the edge of the irradiation target is defined on a slice plane basis manually by the medical worker and/or automatically by the treatment planning system 60 (step S4), and irradiation conditions (dose, spot position, irradiation angle, or the like) of a charged particle beam are assigned spot by spot for each slice plane (step S5). The treatment planning system 60 generates treatment plan data including information on the irradiation target and the edge thereof and data of a dose, a dose rate, or the like for each irradiation spot and transmits the information and the data to the irradiation pattern converting device 70 (step S6). Note that the order of steps S2 to S5 is not limited to the above and may be changed as appropriate.

The irradiation pattern converting device 70 generates irradiation control data based on the treatment plan data received from the treatment planning system 60 and transmits the generated irradiation control data to the irradiation control device 80 (step S7). The irradiation control device 80 controls the accelerator 20, the charged particle beam transport system 30, the focusing magnet 40, the irradiation nozzle 50, and the collimator apparatus 100 to control charged particle beam irradiation to the irradiation target by performing scanning irradiation based on the irradiation control data received from the irradiation pattern converting device 70, and irradiation treatment with a charged particle beam to the irradiation target is started (step S8).

Figure 7:
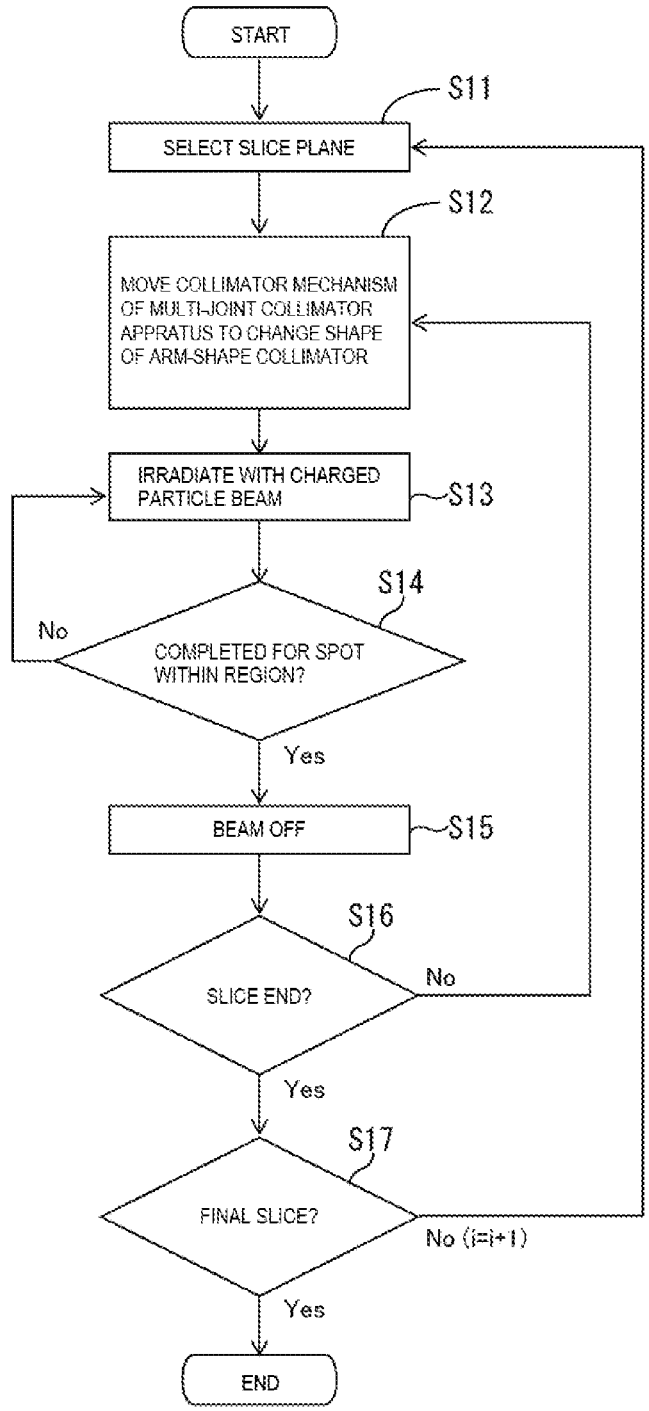
FIG. 7 is a control flowchart after irradiation treatment by using a charged particle beam is started.

FIG. 7 is a control flowchart after irradiation treatment with a charged particle beam is started by the irradiation control device 80.

The irradiation control device 80 selects the i-th slice plane (i is an integer from 1 to the total number of slice planes) of an irradiation target to be irradiated with a charged particle beam (step S11).

The collimator control unit 82 of the irradiation control device 80 moves the collimator mechanism 102 of the collimator apparatus 100 to the edge of the irradiation target on the YZ plane based on information (such as information on the position coordinates or the shape) at the edge of the irradiation target on the i-th slice plane, adjusts the positions of the base part 106 or the arm-shape collimators 110 and 120 of the collimator mechanism 102 so as to be able to block a charged particle beam spreading out of the edge, and moves the orientation of each movable leaf of the arm-shape collimators 110 and 120 to be adjusted into the shape in accordance with the shape of the edge (step S12). Note that the edge may be the whole edge of an irradiation target on the i-th slice plane or may be a part of the edge of the irradiation target.

While scanning a region including the edge of the irradiation target (including a case of the whole irradiation target) on the i-th slide plane, the irradiation control device 80 irradiates each irradiation spot within the region with a charged particle beam (step S13). Step S13 is repeated until irradiation with a charged particle beam ends for all the irradiation spots within the region (step S14, No).

If the irradiation with a charged particle beam ends for all the irradiation spots within the region (step S14, Yes), the irradiation control device 80 stops the irradiation with a charged particle beam (step S15) and determines whether or not irradiation with a charged particle beam has been performed for all the irradiation spots of the irradiation target on the i-th slice plane (step S16).

If the irradiation with a charged particle beam has not been performed for all the irradiation spots of the irradiation target on the i-th slice plane (step S16, No), the collimator mechanism 102 of the collimator apparatus 100 is moved to an edge of another part of the irradiation target, and steps S12 to S16 are then repeated.

If the irradiation with a charged particle beam has been performed for all the irradiation spots of the irradiation target on the i-th slice plane (step S16, Yes), the irradiation control device 80 determines whether or not irradiation with a charged particle beam is completed for all the slice planes (step S17). If the irradiation is not completed (step S17, No), the (i+1)-th slice plane is selected (step S11), and the process of steps S12 to S16 is performed. If the process is completed for all the slice planes (step S17, Yes), the irradiation treatment with a charged particle beam ends.

The charged particle irradiation apparatus according to the present embodiment has one or more collimator apparatuses 100 (100a, 100b) in the irradiation nozzle 50, and the collimator mechanism 102 of the collimator apparatus 100 has at least one arm-shape collimator 110 (and 120) extending from the base part 106. The arm-shape collimator has a plurality of movable leaves that are connected in series and move independently of each other, respective movable leaves move independently on the XY plane perpendicular to the traveling direction of the charged particle beam, and the arm-shape collimator 110 (and 120) changes the shape thereof along the shape of the edge of the irradiation target. Accordingly, when the edge of the irradiation target is irradiated with a charged particle beam by scanning irradiation, it is prevented that the outside of the irradiation target is irradiated with the charged particle beam, and this improves the sharpness of the dose distribution of the charged particle beam at the edge of the irradiation target.

Figure 12A:
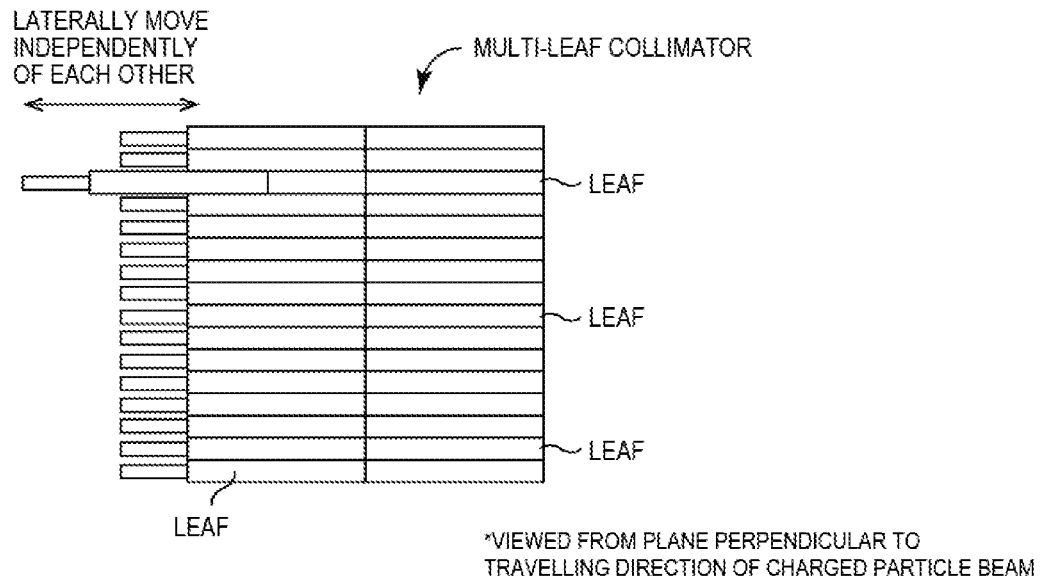
FIG. 12A and FIG. 12B are schematic diagrams of a configuration of a multi-leaf collimator of a conventional art.
Figure 12B:
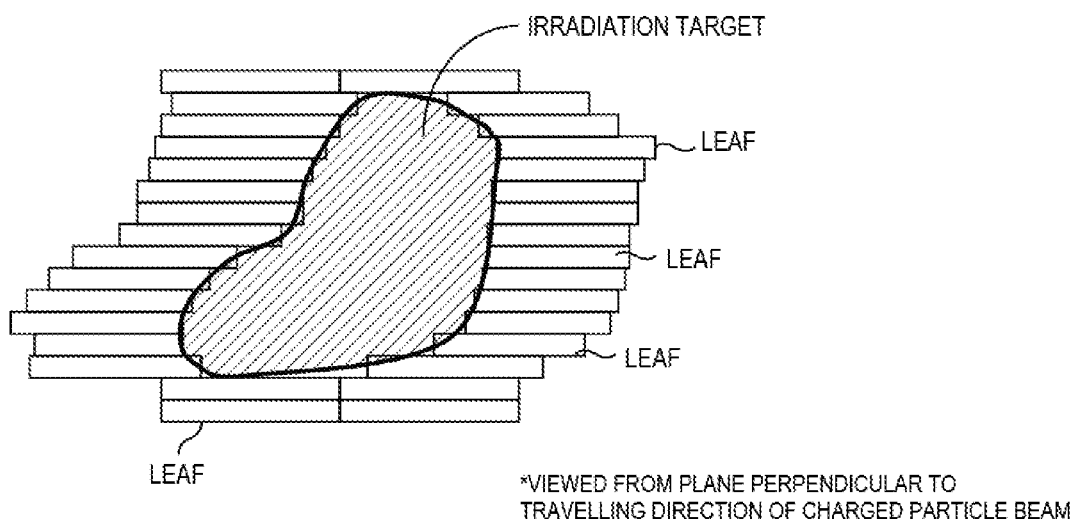

Further, in the configuration of the conventional multi-leaf collimator as illustrated in FIG. 12, it is required to be formed of a large number of leaves that cover the whole irradiation target and control and drive respective leaves independently on a plane perpendicular to the traveling direction of a charged particle beam. In such a configuration, there is a problem of significantly large scaled collimator configuration because each leaf has a large size or weight. In the collimator apparatus 100 according to the present embodiment, however, this problem of the conventional technology is solved.

Second Embodiment

Figure 8A:
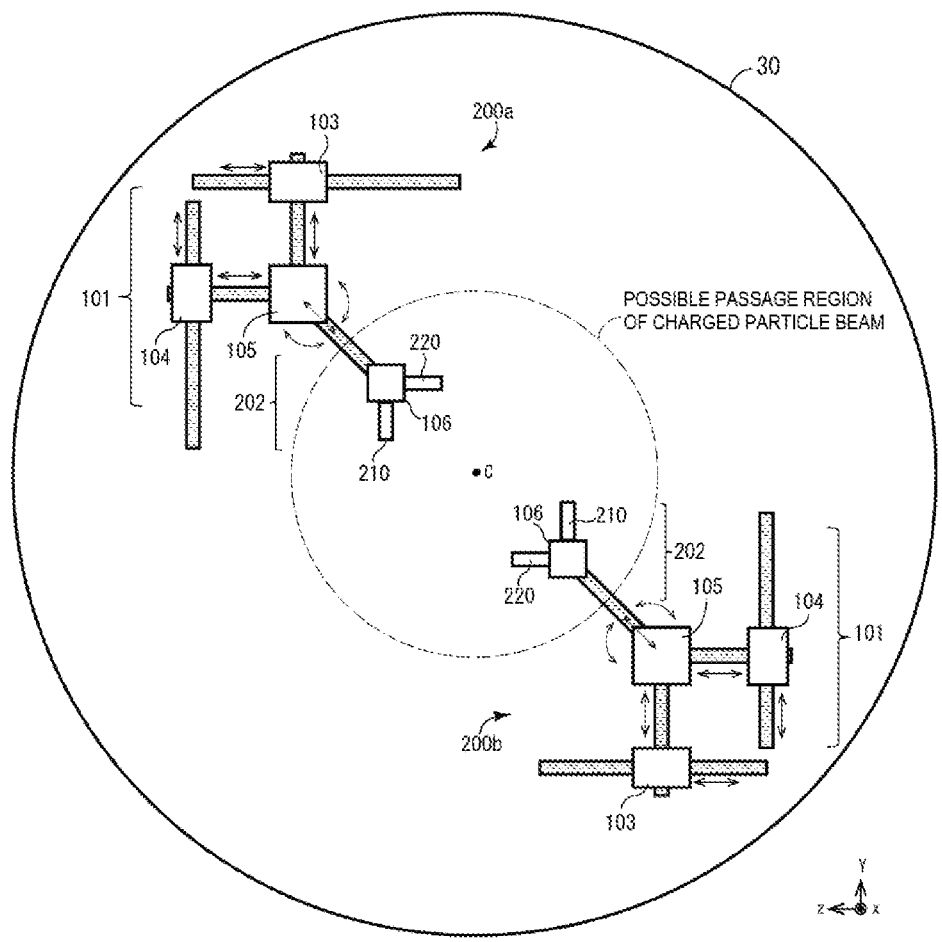
FIG. 8A and FIG. 8B are schematic diagrams of a configuration of a collimator apparatus in a second embodiment.

A charged particle irradiation apparatus according to the second embodiment of the present invention has a collimator apparatus 200 in the irradiation nozzle 50, and the collimator apparatus 200 is formed of a first collimator apparatus 200a and a second collimator apparatus 200b (FIG. 8).

A collimator mechanism 202 of each of the first and second collimator apparatuses 200a and 200b has arm-shape collimators 210 and 220 extending from the base part 106, and each of the arm-shape collimators 210 and 220 has a single movable leaf. Note that description for the same configuration as that in the first embodiment will be omitted as appropriate. Further, in the same manner as in the first embodiment, the collimator apparatus 200 may have only one collimator apparatus 200 or may have three or more collimator apparatuses 200.

Figure 8B:
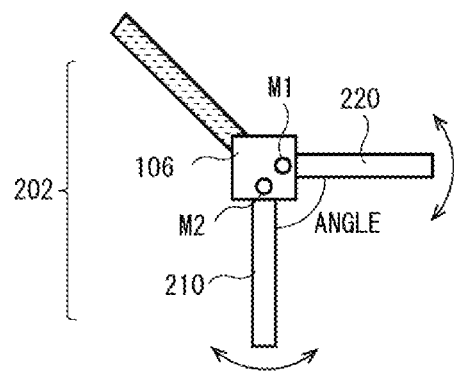

As illustrated in FIG. 8B, the arm-shape collimators 210 and 220 of the collimator mechanism 202 of the collimator apparatus 200 are configured to rotate independently of each other by being driven by the actuators M1 and M2, respectively, on the YZ plane perpendicular to the traveling direction of a charged particle beam. Although FIG. 8 illustrates a form in which the angle between the arm-shape collimators 210 and 220 is approximately 90 degrees, the angle between the arm-shape collimators 210 and 220 can be adjusted to any angle from 0 to 360 degrees.

In the present embodiment, the collimator mechanism 202 of the collimator apparatus 200 is configured to move to follow a scan of charged particle beam irradiation at the edge of an irradiation target. The number of movable leaves forming the arm-shape collimators 210 and 220 is reduced as small as possible, thereby the weight of the collimator mechanism 202 is reduced so that the collimator mechanism 202 can move to follow a scan of charged particle beam irradiation, and accordingly the collimator mechanism 202 is configured to follow a relatively fast scan of charged particle beam irradiation.

Blocking of a charged particle beam that would otherwise irradiate the outside of the edge of an irradiation target will be described in the present embodiment with reference to FIG. 9.

On the YZ plane, when the edge (at the upper left viewed from the front of the drawing sheet) of the irradiation target is irradiated with a charged particle beam, if the collimator apparatus 200a were not present, a part of the distribution of the charged particle beam would also irradiate the outside of the edge of the irradiation target due to spread of the charged particle beam (spread of the dose distribution).

Figure 9A:
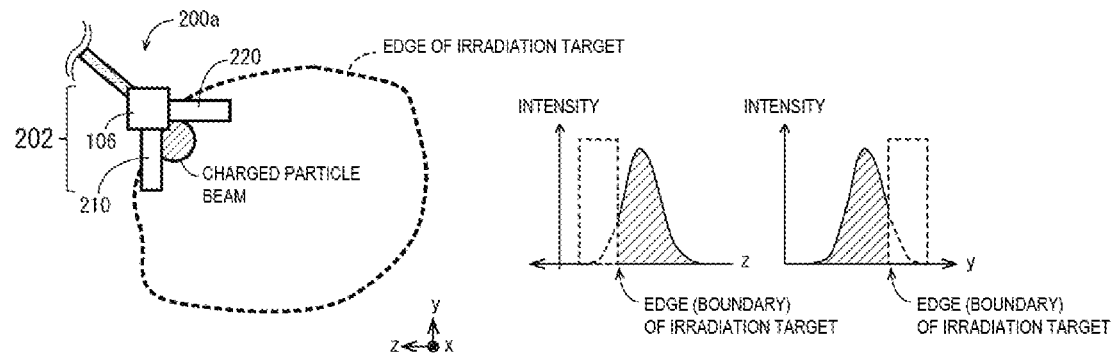
FIG. 9A to FIG. 9C are diagrams illustrating that a dose distribution is blocked by the collimator apparatus.

In FIG. 9A, the collimator mechanism 202 of the collimator apparatus 200a is arranged at the edge of an irradiation target, the angle between the movable leaves is adjusted (or maintained at a pre-defined angle) along the shape of the edge, and a charged particle beam that would otherwise irradiate the outside of the edge is blocked as seen in a graph illustrated in the right side in FIG. 9A.

Figure 9B:
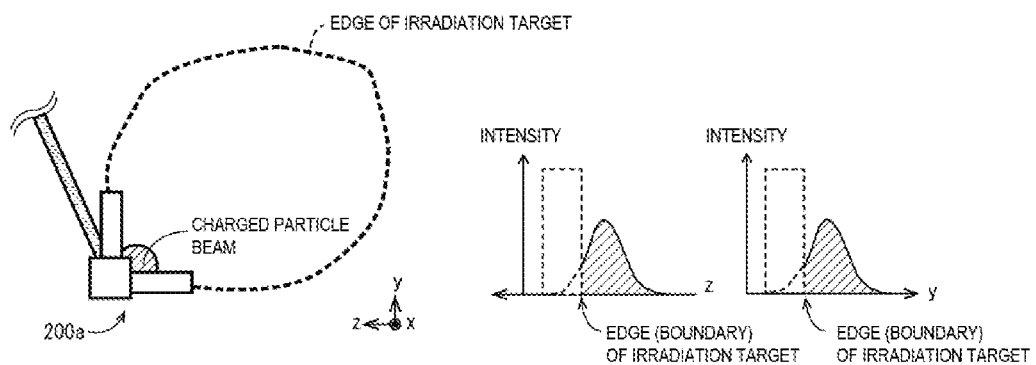
Figure 9C:
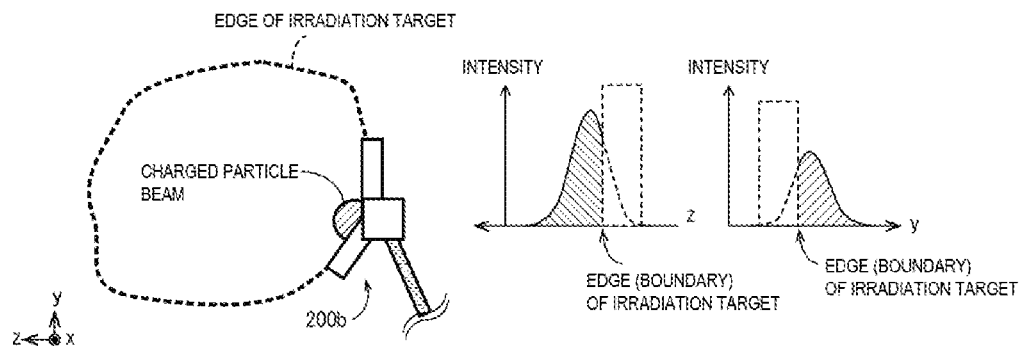

Similarly, in FIG. 9B, the collimator mechanism 202 of the collimator apparatus 200a is arranged at the edge of an irradiation target, and a charged particle beam that would otherwise irradiate the outside of the edge is blocked as seen in a graph illustrated in the right side in FIG. 9B. Further, in FIG. 9C, the collimator mechanism 202 of the collimator apparatus 200b moves at the edge of the irradiation target and adjusts the angle between the movable leaves (or maintains a pre-defined angle) along the shape of the edge, and thereby, a charged particle beam that would otherwise irradiate the outside of the edge is blocked as seen in a graph illustrated in the right side in FIG. 9C.

A configuration in which the collimator mechanism 202 of the collimator apparatus 200 of the present embodiment moves to follow a scan of a charged particle beam at the edge of an irradiation target will be described with reference to FIG. 10.

In the collimator control unit 82 of the irradiation control device 80, when the edge of an irradiation target is irradiated spot by spot based on information on the irradiation position of a charged particle beam and information on the edge of the irradiation target, the collimator mechanism 202 of the collimator apparatus 200 moves to (near) the position of the irradiation spot, and the angle between the movable leaves 210 and 220 is adjusted (or maintained at a pre-defined angle without being adjusted) along the shape of the edge. In such a way, when irradiating the edge of an irradiation target with a charged particle beam, the collimator control unit 82 of the irradiation control device 80 also controls a collimator mechanism 202 to move to follow the position of the irradiation.

For example, when a scan of an irradiation spot is started from the edge of an irradiation target, the collimator mechanism 202 of the collimator apparatus 200 moves to the position of the irradiation spot, the angle between the movable leaves 210 and 220 is adjusted along the shape of the edge (or maintained at a pre-defined angle without being adjusted), and a charged particle beam that would otherwise irradiate the outside of the edge is blocked (FIG. 10A). In a scan of the edge of an irradiation target with charged particle beam irradiation, as illustrated in FIGS. 10B and 10C, the collimator mechanism 202 also moves to follow the motion on irradiation spots, the angle between the movable leaves 210 and 220 is also adjusted, and a charged particle beam that would otherwise irradiate the outside of the edge is blocked. On the other hand, when the irradiation spot of the charged particle beam is not at the edge of the irradiation target, the collimator mechanism 202 is not required to and thus does not perform the follow-up operation (FIG. 10D). Note that the collimator mechanism 202 may be controlled to perform the follow-up operation. Further, once the irradiation spot of the charged particle beam comes to the edge of the irradiation target, the follow-up operation of the collimator mechanism 202 is performed (FIG. 10E). Further, the edge is blocked by the second collimator apparatus 200b (FIG. 10F). Note that, in the present embodiment, the angle between the movable leaves 210 and 220 may be changed, or the angle may be fixed at 90 degrees or the like, for example.

As described above, the charged particle irradiation apparatus according to the present embodiment has one or more collimator apparatuses 200 (200a, 200b) in the irradiation nozzle 50, and the collimator mechanism 202 of each collimator apparatus 200 has at least one arm-shape collimator 210 (and 220) extending from the base part 106. The arm-shape collimators each have a single movable leaf (including a case where a plurality of movable leaves are combined to form a single movable leaf), the movable leaves move independently, respectively, on the XY plane perpendicular to the traveling direction of a charged particle beam, and the arm-shape collimator 210 (and/or 220) changes the shape thereof along the shape of the edge of an irradiation target (note that a case where the shape of the arm-shape collimator is not changed for blocking is included). Further, the collimator mechanism 202 moves to follow scanning irradiation (a scan of irradiation spots) at least at the edge of the irradiation target. Therefore, when the edge of the irradiation target is irradiated with a charged particle beam, it is prevented that the outside of the irradiation target is irradiated with the charged particle beam, and this improves the sharpness of the dose distribution of the charged particle beam at the edge of the irradiation target.

Third Embodiment

A charged particle irradiation apparatus according to the third embodiment of the present invention has a collimator apparatus 300 in the irradiation nozzle 50, and a collimator mechanism 302 of the collimator apparatus 300 has a base part 306 and arm-shape collimators 310 and 320 extending from the base part 306. Although each of the arm-shape collimators 310 and 320 has a plurality of movable leaves, unlike the first embodiment, a plurality of the movable leaves are provided arranged in the traveling direction (the X-axis direction) of a charged particle beam. Further, each movable leaf has one or more joint parts 315 in which an actuator such as a motor is embedded so that a charged particle beam can pass through an opening that is as if made with human fingers, and the shape of an opening made with the movable leaves can be changed also in the traveling direction of the charged particle beam.

Figure 11A:
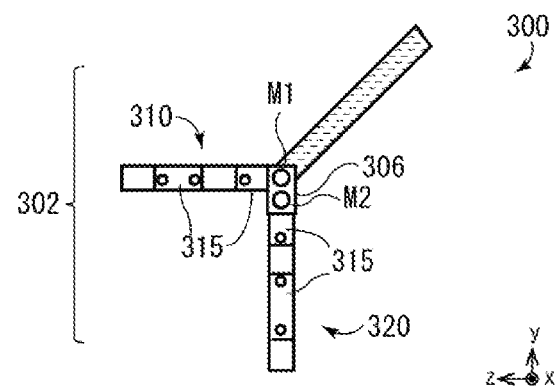
FIG. 11A to FIG. 11C are schematic diagrams of a configuration of a collimator apparatus in a third embodiment.
Figure 11B:
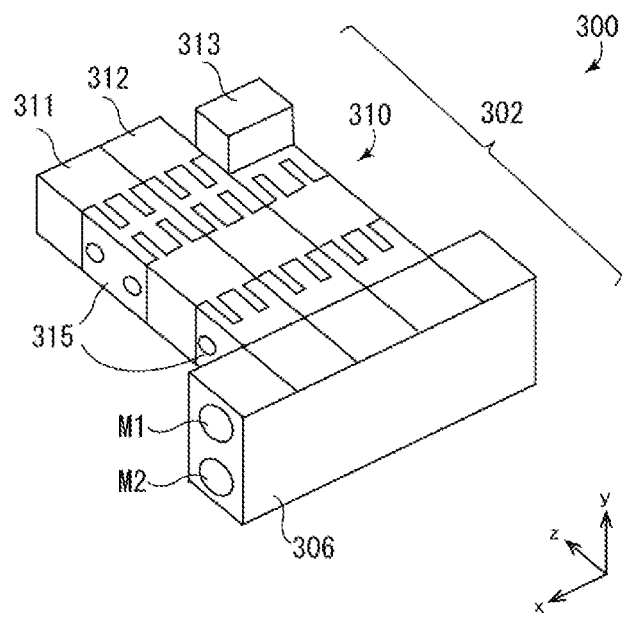

FIG. 11A illustrates the collimator mechanism 302 of one collimator apparatus 300, and the drive mechanism thereof (not illustrated) is the same as that in the first and second embodiments. The collimator mechanism 302 has the base part 306 and the arm-shape collimators 310 and 320 extending from the base part 306. The number of arm-shape collimators may be one or greater. The arm-shape collimator 310 has a plurality of movable leaves 311 to 313 (FIG. 11B), and each of the movable leaves 311 to 313 is configured to be bendable about the joint part 315 on the YZ plane as if each movable leaf is a finger. Note that the same applies to the arm-shape collimator 320, and the illustration and description thereof will be omitted.

Figure 11C:
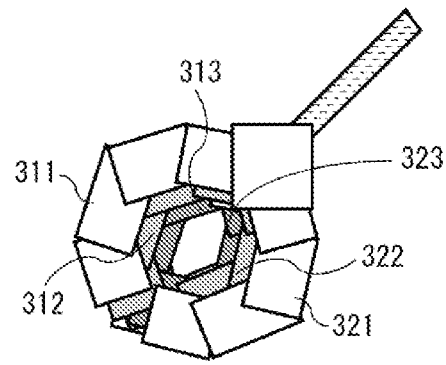

The present embodiment may be configured such that respective movable leaves (311 to 313 and 321 to 323) in the X-axis direction are driven independently of each other and, as illustrated in FIG. 11C, an opening made with the movable leaves 311 and 321 on the incidence side of a charged particle beam is large, an opening made with the movable leaves 312 and 322 is small, and an opening made with the movable leaves 313 and 323 on the exit side of the charged particle beam is smaller, for example. In such a way, when the opening on the incidence side in the traveling direction (the X-axis direction) of a charged particle beam is larger than that on the exit side, the required positional accuracy of the charged particle beam entering a collimator opening made with the movable leaves 311 and 321 can be restrained, and the width (on the YZ plane) of the charged particle beam exiting the opening made with the movable leaves 313 and 323 on the exit side can be reduced. Note that it is preferable that the width (on the YZ plane) of the opening made with the movable leaves 313 and 323 be smaller than the width of the dose distribution (on the YZ plane) of a charged particle beam.

Note that the configuration illustrated in the third embodiment is applicable to the configuration according to the first and second embodiments. That is, in the first and second embodiments, each arm-shape collimator may have a plurality of movable leaves connected to the base part 106 and arranged adjacently in the traveling direction (the X-axis direction) of the charged particle beam, and each movable leaf may have at least one joint part and be configured to be rotatable about the joint part.

In the charged particle irradiation apparatus according to one embodiment of the present invention, the collimator mechanism is moved and/or the movable leaf is rotated so that the arm-shape collimator is arranged along the shape of the edge of an irradiation target on a plane perpendicular to the traveling direction of a charged particle beam to cause the arm-shape collimator to block a charged particle beam that would otherwise irradiate outside of the out of the irradiation target, and this improves the sharpness of a dose distribution at the edge of the irradiation target.

The size, the material, the shape, the relative position of components, or the like described above may be changed in accordance with the structure of the apparatus to which the present invention is applied or various conditions. It is not intended to limit the disclosure to any specific terms used in the description and the embodiments, those skilled in the art can use another equivalent component, and the embodiments described above can be modified and changed differently as long as not departing from the spirit or the scope of the present invention. Further, even if not explicitly described, the feature described in association with one of the embodiments of the present invention can be used together with another embodiment.

The present application is based on and claims priority from Japanese Patent Application No. 2020-148135, filed Sep. 3, 2020, the disclosure of which is hereby incorporated by reference herein in its entirety.

LIST OF REFERENCE SYMBOLS 10 charged particle irradiation apparatus
20 accelerator
30 charged particle beam transport system
31 charged particle beam adjustment unit
32 vacuum chamber
33 bending magnet
34 sector-shaped vacuum chamber
40 focusing magnet
50 irradiation nozzle
52 scanning magnet
54 dose monitor (first dose monitor)
56 position monitor
60 treatment planning system
70 irradiation pattern converting device
80 irradiation control device
82 collimator control unit
100, 200, 300 collimator apparatus
101 drive mechanism
102, 202, 302 collimator mechanism
103 to 105 drive unit
106, 306 base part
110, 120, 210, 220, 310, 320 arm-shape collimator
111 to 114, 311 to 313, 321 to 323 movable leaf
315 joint part

What is claimed is:

1. A charged particle irradiation apparatus that performs a scan with a charged particle beam to irradiate an irradiation target spot by spot, the charged particle irradiation apparatus comprising:
   a collimator apparatus provided in an irradiation nozzle that emits the charged particle beam to the irradiation target; and
   a collimator control unit that controls the collimator apparatus,
   wherein the collimator apparatus comprises
      a collimator mechanism comprising one or more arm-shape collimators extending from a base part, and
      a drive mechanism that moves the collimator mechanism on a plane (YZ plane) perpendicular to a traveling direction (X-axis direction) of the charged particle beam,
   wherein each of the arm-shape collimators comprises a plurality of movable leaves that rotate independently of each other on the perpendicular plane (YZ plane), and
   wherein by moving the collimator mechanism and/or rotating the movable leaves so that the one or more arm-shape collimators are arranged along a shape of an edge of the irradiation target on the perpendicular plane (YZ plane), the collimator control unit causes the one or more arm-shape collimators to block the charged particle beam that would otherwise irradiate outside of the edge of the irradiation target.

2. The charged particle irradiation apparatus according to claim 1,
   wherein the one or more arm-shape collimators comprise at least two arm-shape collimators extending from the base part, and each of the arm-shape collimators comprises a plurality of the movable leaves connected to each other in series, and
   wherein by moving the collimator mechanism and/or rotating the movable leaves, respectively, so that the arm-shape collimators are arranged along the shape of the edge of the irradiation target, the collimator control unit causes the one or more arm-shape collimators to block the charged particle beam that would otherwise irradiate outside of the edge of the irradiation target.

3. The charged particle irradiation apparatus according to claim 2,
   wherein the charged particle irradiation apparatus comprises at least two of the collimator apparatuses, and
   wherein by moving the collimator mechanisms, respectively, and/or rotating the movable leaves, respectively, so that each of the arm-shape collimators of the collimator apparatuses are arranged in cooperation along a whole shape of the edge of the irradiation target, the collimator control unit causes each of the arm-shape collimators to block the charged particle beam that would otherwise irradiate outside of the edge of the irradiation target.

4. The charged particle irradiation apparatus according to claim 1,
   wherein the plurality of movable leaves are connected to the base part and arranged adjacently in the traveling direction (X-axis direction), and
   wherein each of the movable leaves has at least one joint part and is configured to rotate about the joint part.

* * * * *